United States Patent [19]

Kawata

[11] Patent Number: 5,244,384
[45] Date of Patent: Sep. 14, 1993

[54] DENTAL HANDPIECE APPARATUS HAVING HEATING UNIT

[75] Inventor: Sosaku Kawata, Kanuma, Japan

[73] Assignee: Nakanishi Dental Mfg. Co., Ltd., Tochigi, Japan

[21] Appl. No.: 925,854

[22] Filed: Aug. 6, 1992

[30] Foreign Application Priority Data

Aug. 7, 1991 [JP] Japan .................................. 3-197835

[51] Int. Cl.$^5$ ............................................. A61C 3/00
[52] U.S. Cl. ........................................ 433/32; 433/98
[58] Field of Search ........................... 433/32, 98, 101

[56] References Cited

U.S. PATENT DOCUMENTS

| | | | |
|---|---|---|---|
| 3,005,261 | 10/1961 | Haller | 433/32 |
| 3,094,779 | 6/1963 | Boulsover et al. | 433/32 |
| 3,169,318 | 2/1965 | Oaks | 433/32 |
| 4,201,051 | 5/1980 | Hall | 433/101 |
| 5,061,178 | 10/1991 | Ueno | 433/32 |
| 5,123,839 | 6/1992 | West | 433/32 |

*Primary Examiner*—John J. Wilson
*Attorney, Agent, or Firm*—Malcolm B. Wittenberg

[57] ABSTRACT

A dental handpiece apparatus having a heating unit contains a liquid supply source, liquid flow passages for ejecting a liquid from the liquid supply source at an ejection passage provided at a distal end of a main body of a handpiece, a gas supply source, gas flow passages for ejecting a gas from the gas supply source at the ejection passage and a heating unit provided in at least one the liquid flow passages and the gas flow passages for heating at least one of the liquid and the gas.

8 Claims, 2 Drawing Sheets

DENTAL HANDPIECE APPARATUS HAVING HEATING UNIT

BACKGROUND OF THE INVENTION

The present invention relates to a dental handpiece apparatus having a heating unit therein.

A dental handpiece apparatus employed in dental treatment is provided with cooling means, such as means for spraying water from a head part of the handpiece to a site of treatment for preventing the site of treatment from being heated due to cutting when cutting a tooth with the aid of the dental handpiece apparatus. However, with the conventional cooling means, since water at a lower temperature, such as tap water, is directly supplied to the site of treatment, the cut part of the tooth smarts with cold water to increase the pain felt by the patient. If the water is heated and maintained in the heated state at the supply source, a larger quantity of electric power is consumed, while the apparatus is increased in size. Besides, the cut part of the tooth similarly smarts with cold air sprayed from the head of the handpiece to the cut part of the tooth for scattering the debris of the cut tooth.

SUMMARY OF THE INVENTION

It is therefore an object of the present invention to provide a dental handpiece apparatus having a heating unit in which the fluid ejected from the distal end of the handpiece may be heated in a simple manner and at a reduced power consumption for alleviating the smarting pain felt by the patient at the time of tooth cutting.

The above and other objects of the invention will become apparent from the following description.

According to the presence invention, there is provided a dental handpiece apparatus having a heating unit, the apparatus comprising a liquid supply source, liquid flow passages for ejecting a liquid from the liquid supply source at an ejection passage provided at a distal end of a main body of the handpiece, a gas supply source, gas flow passages for ejecting a gas from the gas supply source at the ejection passage, and a heating unit provided in at least one of the liquid flow passages and the gas flow passages for heating at least one of the liquid and the gas.

PREFERRED EMBODIMENTS OF THE INVENTION

Figure 1:
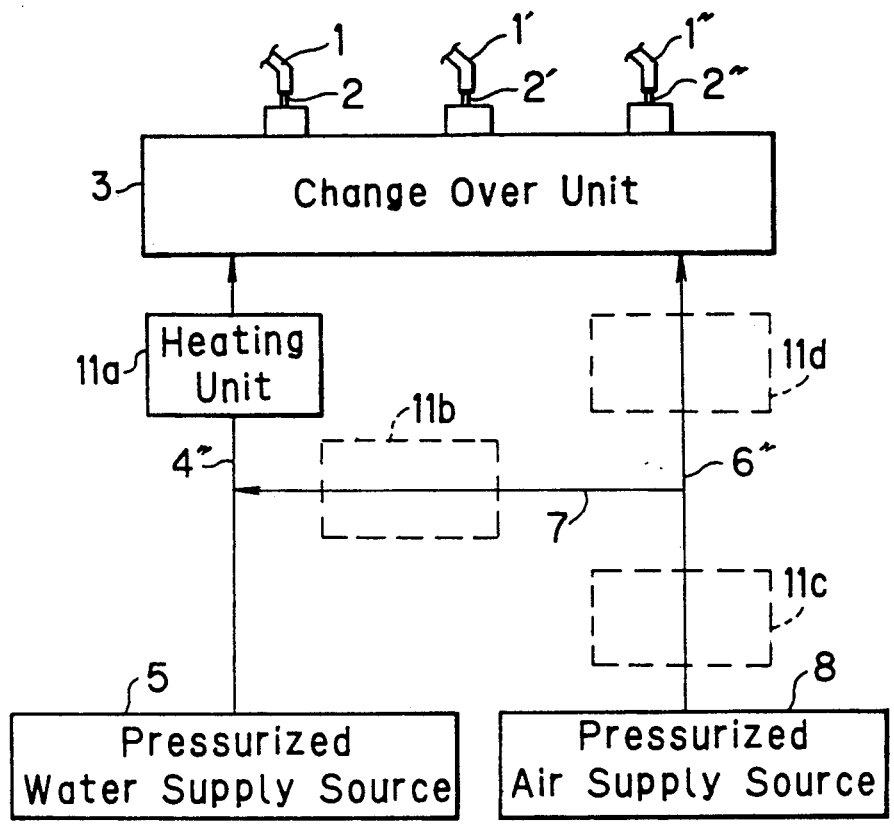
FIG. 1 is a flow circuit diagram showing a dental handpiece apparatus according to an embodiment of the present invention.
Figure 2:
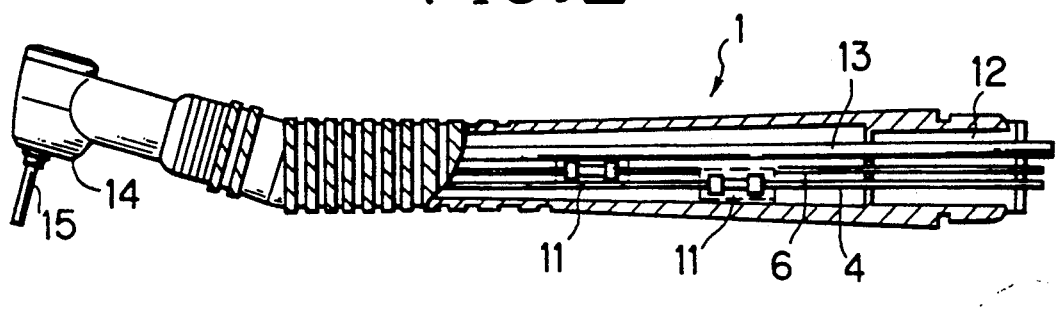
FIG. 2 is a partially fragmentary side view showing a dental handpiece apparatus fitted with a heating unit according to a modified embodiment of the present invention.
Figure 3:
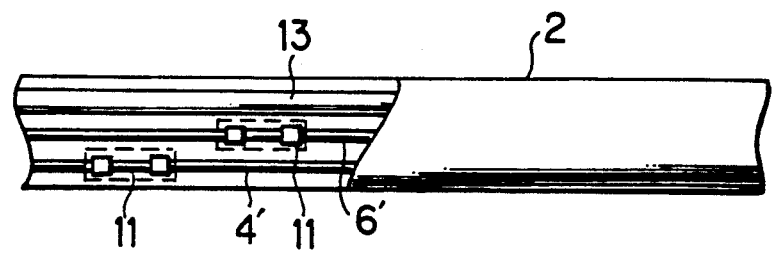
FIG. 3 is a partially fragmentary side view showing a connecting hose fitted with a heating unit according to another modified embodiment of the present invention.

Referring to FIGS. 1 to 3, a water channel 4 (FIG. 2) is enclosed within each of handpieces 1, 1' and 1", and another water channel 4' (FIG. 3) is enclosed within each of connecting hoses 2, 2' and 2" and is connected to a changeover unit 3. Water pressurized by a pressurized water supply source 5 is supplied via a further water channel 4" to the changeover unit 3 so as to be supplied via connecting hoses 2, 2' or 2" to a desired one of the handpieces 1, 1' or 1" at the option of a dentist. The water so supplied is ejected via an ejecting passage 14 (FIG. 2) formed at a head of the selected handpiece, such as the handpiece 1.

An air flow passage 6 (FIG. 2) is enclosed within each of handpieces 1, 1' and 1", and another air flow passage 6' (FIG. 3) is enclosed within each of connecting hoses 2, 2' and 2" and is connected to the changeover unit 3. Air pressurized by a pressurized air supply source 8 is supplied via a further air passage 6' to the changeover unit 3 so as to be supplied via the connecting hoses 2, 2' or 2" to a desired one of the handpieces 1, 1' or 1" at the option of a dentist. The air so supplied is passed to the ejecting passage 14 at the head of the handpiece 1 (FIG. 2). The air flow passage 6" is branched and connected via an air flow passage 7 to the water channel 4" by means of which an air/water mixture is ejected, as needed, at the ejection passage 14 (FIG. 2) at the head of the handpiece 1.

Figure 4A:
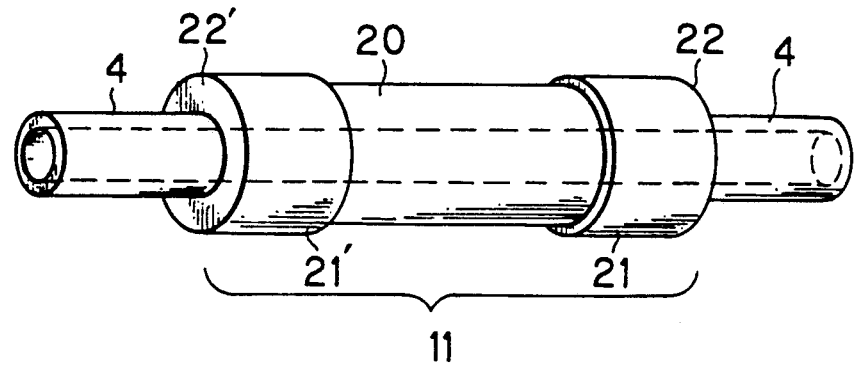
FIGS. 4(A) and 4(B) are an enlarged perspective view and an enlarged exploded perspective view of the heating unit, respectively.
Figure 4B:
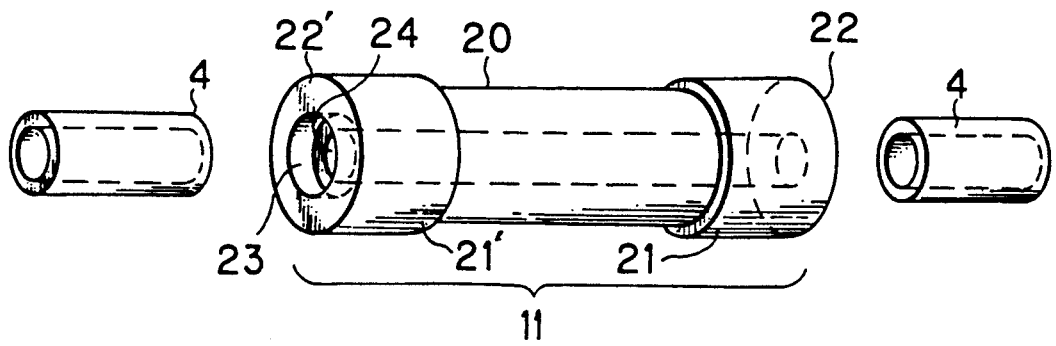

According to the present invention, a heating unit 11 shown in FIGS. 4A and 4B is employed. The heating unit 11 is tubular, as shown in FIG. 4A, and includes a ceramic heating element 20 on both sides of which electrodes 21, 21' are mounted for clamping the heating element 20. End faces 22, 22' of the electrodes 21, 21' are formed with recesses 23 engaged by any of the water channels 4, 4' or 4" or by any of the air flow passages 6, 6' or 6". The heating unit 11 has a bore 24 of the same diameter as that of the water channels or the air flow passages. An electrical wiring to the heating unit 11 my be made by utilizing an electrical connection, not shown, for an incandescent lamp or the like, also not shown, adapted for supplying the light to an optical fiber when the heating unit is mounted within such a dental handpiece. Although a ceramic heater is employed in the illustrated embodiment, a coil heater may be similarly employed. The water or air is preferably heated by the heating unit to a temperature in a range of from 20° to 40° C., that is a temperature close to the body temperature, for alleviating the pain felt by the patient during dental treatment. The temperature may be adjusted by a voltage controller, not shown, provided at a handpiece hose coupling.

In FIG. 1, a heating unit 11a is shown by a solid line as being provided within the water channel 4". However, at least one of heating units 11b, 11c and 11d may be provided in the air flow passage 7 and/or in the air flow passage 6".

FIG. 2 shows a modification of the present invention in which the heating unit 11 is provided in each of the water channel 4 and the air flow passage 6. The handpiece 1 is provided with an air duct 13 for supplying air used for rotating an air turbine, not shown, provided within a main body of the handpiece 1, a joint 12 for connecting the handpiece to the connecting hose 2, and the water channel 4 as well as the air flow passage 6 communicating with the ejection passage 14. It is within the water channel 4 and the air flow passage 6 that the heating units 11 are provided. In this manner, the water and the air, which are at ambient temperature at a time point when they are supplied to the handpiece, may be heated to a moderate temperature for being ejected at the ejection passage 14 for dental treatment.

FIG. 3 shows a further modification of the present invention in which the heating unit 11 is provided in each of the water channel 4' and the air flow passage 6' within the connecting hose 2. Referring to FIG. 3, the connecting hose 2 includes an air duct 13, the water channel 4' and the air flow passage 6'. It is within the water channel 4' and the air flow passage 6' that the heating units 11 are provided. In this manner, the water and the air, which are at ambient temperature at the time point when they are supplied to the connecting hose 2, may be heated to a moderate temperature by the heating units 11 before being ejected at the ejecting passage 14.

With the dental handpiece according to the present invention, by providing a heating unit in at least one of the water channels and the air flow passages, dental treatment may be achieved with reduced power consumption and with a minimum size of the apparatus without imparting excessive pain to the patient.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece apparatus having a heating unit, said apparatus comprising:
    a liquid supply source,
    liquid flow passages for ejecting a liquid from said liquid supply source at an ejection passage provided at a distal end of a main body of a handpiece,
    a gas supply source,
    gas flow passages for ejecting a gas from said gas supply source at said ejection passage and
    a heating unit provided in at least one of said liquid flow passages and said gas flow passages for heating at least one of the liquid and the gas, said heating unit having a tubular ceramic heating element and electrodes provided on said tubular ceramic heating element, and said tubular ceramic heating element enclosing at least one of said liquid flow passages and said gas flow passages.

2. An apparatus according to claim 1 wherein said liquid flow passages include a first liquid supply passage for supplying the liquid to a changeover unit adapted for selectively supplying the liquid to one of a plurality of the main bodies of the handpieces and wherein said heating unit is provided in said first supply passage.

3. An apparatus according to claim 2 wherein an additional gas flow passage is provided for supplying the gas from said gas supply source to said first liquid supply passage and wherein said heating unit is provided in said additional gas flow passage.

4. An apparatus according to claim 1 wherein said gas flow passages include a first gas supply passage for supplying the gas to a changeover unit adapted for selectively supplying the gas to one of a plurality of the main bodies of the handpieces and wherein said heating unit is provided in said first gas supply passage.

5. An apparatus according to claim 1 wherein said liquid flow passages include a second liquid supply passage provided in a connecting hose adapted for supplying the liquid from a changeover unit adapted for selectively supplying to one of a plurality of said main bodies of the handpieces and wherein said heating unit is provided within said second liquid supply passage.

6. An apparatus according to claim 1 wherein said gas flow passages include a second gas supply passage provided in a connecting hose adapted for supplying the gas from a changeover unit adapted for selectively supplying the gas to one of a plurality of said main bodies of the handpieces and wherein said heating unit is provided within said second gas supply passage.

7. An apparatus according to claim 1 wherein said liquid flow passages include a third liquid supply passage provided within the main body of the handpiece and wherein said heating unit is provided within said third liquid supply passage.

8. An apparatus according to claim 1 wherein said gas flow passages include a third gas supply passage provided within the main body of the handpiece and wherein said heating unit is provided within said third gas supply passage.

* * * * *